United States Patent
Baturin

(10) Patent No.: US 10,236,091 B2
(45) Date of Patent: Mar. 19, 2019

(54) BACKSCATTER SHIELDS AND METHODS OF SHIELDING

(71) Applicant: Carestream Health, Inc., Rochester, NY (US)

(72) Inventor: Pavlo Baturin, Santa Clara, CA (US)

(73) Assignee: Carestream Health, Inc., Rcohester, NY (US)

(*) Notice: Subject to any disclaimer, the term of this patent is extended or adjusted under 35 U.S.C. 154(b) by 0 days.

(21) Appl. No.: 15/648,582

(22) Filed: Jul. 13, 2017

(65) Prior Publication Data

US 2018/0019035 A1 Jan. 18, 2018

Related U.S. Application Data

(60) Provisional application No. 62/362,096, filed on Jul. 14, 2016.

(51) Int. Cl.
| | |
|---|---|
| G21K 1/10 | (2006.01) |
| G21K 1/12 | (2006.01) |
| G01T 1/24 | (2006.01) |
| A61N 5/10 | (2006.01) |
| G01T 1/20 | (2006.01) |

(52) U.S. Cl.
CPC .......... G21K 1/12 (2013.01); G01T 1/244 (2013.01); G21K 1/10 (2013.01); A61N 2005/1094 (2013.01); G01T 1/2018 (2013.01)

(58) Field of Classification Search
CPC ... G21K 1/10; G21K 1/12; G01T 1/00; G01T 1/16; G01T 1/20; G01T 1/2006; G01T 1/24; G01T 1/244
See application file for complete search history.

(56) References Cited

U.S. PATENT DOCUMENTS

| | | | | |
|---|---|---|---|---|
| 6,388,250 B1* | 5/2002 | Croydon | ................. | G01T 1/026 250/252.1 |
| 6,548,815 B1* | 4/2003 | Umazaki | ........... | H01L 27/14623 250/370.09 |
| 6,888,144 B2* | 5/2005 | Rodricks | ................... | G01T 1/16 250/370.09 |
| 2014/0291531 A1* | 10/2014 | Dai | ......................... | G01T 1/167 250/366 |

OTHER PUBLICATIONS

J. L. Gaines et al., Scattering of x rays from low-Z materials, Aug. 1, 1980, Lawrence Livermore Laboratory, Manuscript, 17 pages.

* cited by examiner

*Primary Examiner* — Eliza Osenbaugh-Stewart

(57) ABSTRACT

A DR detector having a layer of imaging pixels and one or more shield layers behind the layer of imaging pixels. A first shield layer may have a thickness selected to be between about 1 mil and about 5 mils of a material selected from lead, tungsten, tin, copper, aluminum, and magnesium, selected according to an energy magnitude of radiographic energy received by the detector. A second shield layer may be positioned behind the first shield layer. The second shield layer may have a similar or different thickness selected according to an energy magnitude of radiographic energy received by the detector. The first shield layer may be positioned directly behind the layer of imaging pixels and the second shield layer may be positioned at an interior surface of the back of the detector housing.

19 Claims, 11 Drawing Sheets

BACKSCATTER SHIELDS AND METHODS OF SHIELDING

CROSS REFERENCE TO RELATED APPLICATIONS

This application claims priority to U.S. Patent Application Ser. No. 62/362,096, filed Jul. 14, 2016, in the name of Pavlo Baturin, and entitled BACKSCATTER SHIELD AND METHODS OF SHIELDING, which is hereby incorporated by reference herein in its entirety.

BACKGROUND OF THE INVENTION

The subject matter disclosed herein relates to digital radiographic (DR) detectors. In particular to structures of x-ray backscatter shields and methods of backscatter shielding.

Recent development efforts in the DR detector industry includes two trends: i) reduction of detector weight and ii) reduction of detector thickness. One common approach is thinning of the backscatter shield. Although detector thickness and weight can be reduced this way, the flux of backscattered and reemitted photons from exterior objects making their way back to the scintillator can increase due to thinner shield protection. The effect can become amplified in the case of a collimated beam, where the X-ray beam is directly incident on an exterior area. The backscattered and reemitted (for example via characteristic radiation) photons enter the detector from the back side and pass through internal components making their way back to the scintillator material. This generates a detectable contrast image of internal components, which can have a detrimental effect on image quality.

The discussion above is merely provided for general background information and is not intended to be used as an aid in determining the scope of the claimed subject matter.

BRIEF DESCRIPTION OF THE INVENTION

A DR detector having a layer of imaging pixels and one or more shield layers behind the layer of imaging pixels. A first shield layer may have a thickness selected to be between about 1 mil and about 5 mils of a material selected from lead, tungsten, tin, copper, aluminum, and magnesium, selected according to an energy magnitude of radiographic energy received by the detector. A second shield layer may be positioned behind the first shield layer. The second shield layer may have a similar or different thickness selected according to an energy magnitude of radiographic energy received by the detector. The first shield layer may be positioned directly behind the layer of imaging pixels and the second shield layer may be positioned at an interior surface of the back of the detector housing.

In one embodiment, a DR detector comprises a layer of imaging pixels and a first shield layer behind the layer of imaging pixels. The first shield layer may have a thickness between about 1 mil and about 5 mils of a material selected from lead, tungsten, tin, copper, aluminum, and magnesium, selected according to an energy magnitude of radiographic energy received by the detector to minimize scattered X-ray radiation therewithin. A second shield layer is positioned behind the first shield layer. The second shield layer may have a thickness between about 1 mil and about 5 mils of a material selected from lead, tungsten, tin, copper, aluminum, and magnesium, selected according to an energy magnitude of radiographic energy received by the detector to minimize back-emitted characteristic X-ray radiation therewithin. The first shield layer may be positioned directly behind the layer of imaging pixels and the second shield layer may be positioned at the back of the detector proximate an interior surface of the back of the detector housing.

Disclosed is a backscatter arrangement in an X-ray imaging device, such as a digital flat panel radiographic detector. In one embodiment the arrangement of the backscatter shield aims to reduce both the amount of X-ray radiation scattered and reemitted from the shield itself in the direction of the detector's scintillator material, and the quantity of X-ray radiation scattered and reemitted from regions exterior to the detector and incident back onto the detector. In addition, the embodiments of backscatter shielding described herein are directed to eliminating or reducing structure artifacts in acquired digital images associated with the contrast modulated by electronics and interior components of a detector that have been illuminated by scattered x-ray radiation and secondary radiation from exterior regions.

Disclosed herein is an exemplary backscatter shielding arrangement in an X-ray digital imaging device. The shielding may be made of highly attenuating material, such as lead, and is typically placed behind the pixelated amorphous silicon glass (or any other pixelated substrate) and serves at least two purposes: i) protection of electronic components from radiation damage, and ii) prevention of backscattered and reemitted X-ray radiation from entering into the scintillator material.

To solve the problems described herein, the backscatter shielding may be rearranged. For example, the following rearrangements may be performed:

i) additional filtration can be placed behind the detector;

ii) the shielding behind the substrate glass can be made thinner or removed and additional filtration can be placed behind the detector layers;

iii) total thickness of backscatter shielding can be kept the same, while the shielding behind the glass can be made thinner, while the remaining backscatter material can be moved behind the detector layers.

In the first case, the additional filtration placed behind the detector helps to reduce the flux of backscattered and reemitted photons. It also partially attenuates the backscattered radiation making the spectrum "harder" (i.e., shifted towards the higher energy wavelengths or photons), which reduces the contrast between interior components. One drawback of this arrangement is the increase of detector weight. The second arrangement solves not only the problem of backscattered radiation from exterior regions but additionally reduces the amount of radiation backscattered and reemitted from the shielding located immediately behind the glass. The third arrangement is similar to the second case; however, the total thickness of shielding material would remain the same as it was before rearrangement.

It is possible to use other materials instead of lead. Also, a combination of various materials can be utilized as both shielding behind the glass and shielding behind the detector. To reduce the amount of characteristic radiation entering back to the scintillator, the "behind glass" backscatter shielding can consist of layers of different materials.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 8B is a magnification of the area outlined by the dashed line square of FIG. 8A;

DETAILED DESCRIPTION OF THE INVENTION

Figure 1:
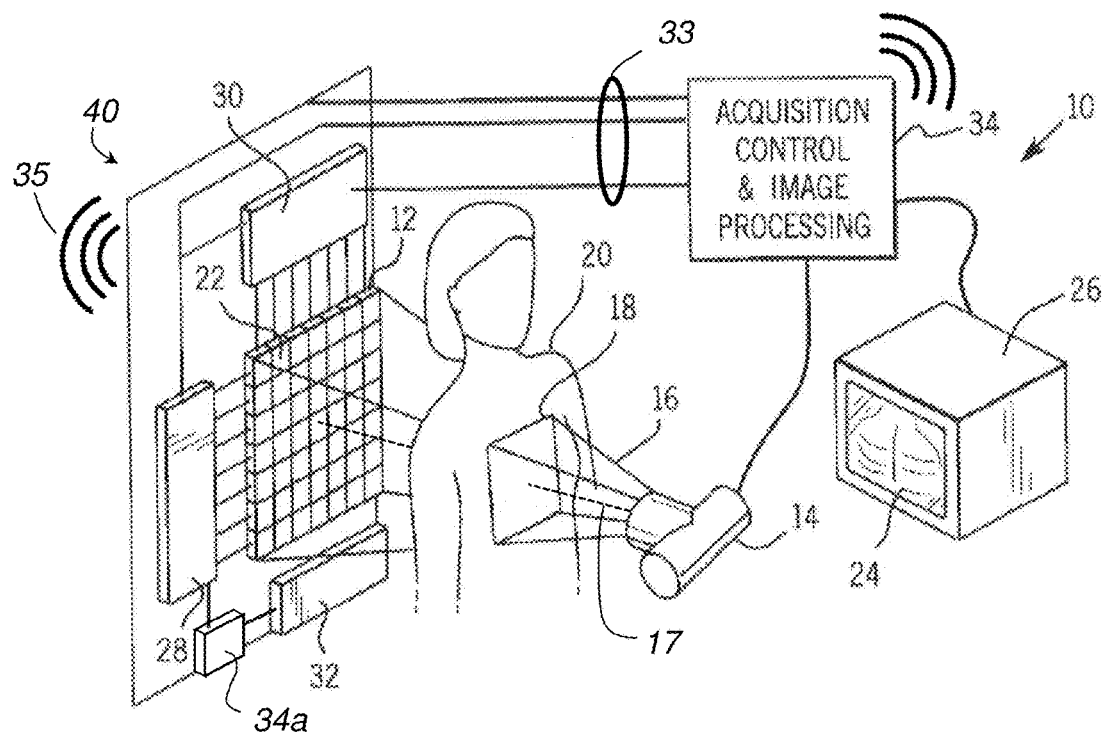
FIG. 1 is a schematic perspective view of an exemplary x-ray system.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) by their position according to column and row. As used herein, the terms "column" and "row" refer to the vertical and horizontal arrangement of the photo sensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g. a brightness level or an amount of energy absorbed by the pixel, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and receiver to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. A portion or all of the acquisition control and image processing unit 34 functions may reside in the detector 40 in an on-board processing system 34a which may include a processor and electronic memory to control operations of the DR detector 40 as described herein, including control of circuits 28, 30, and 32, by use of programmed instructions, and to store and process image data similar to the functions of standalone acquisition control and image processing system 34. The image processing system may perform image acquisition and image disposition functions as described herein. The image processing system 34a may control image transmission and image processing and image correction on board the detector 40 based on instructions or other commands transmitted from the acquisition control and image processing unit 34, and transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

Figure 2:
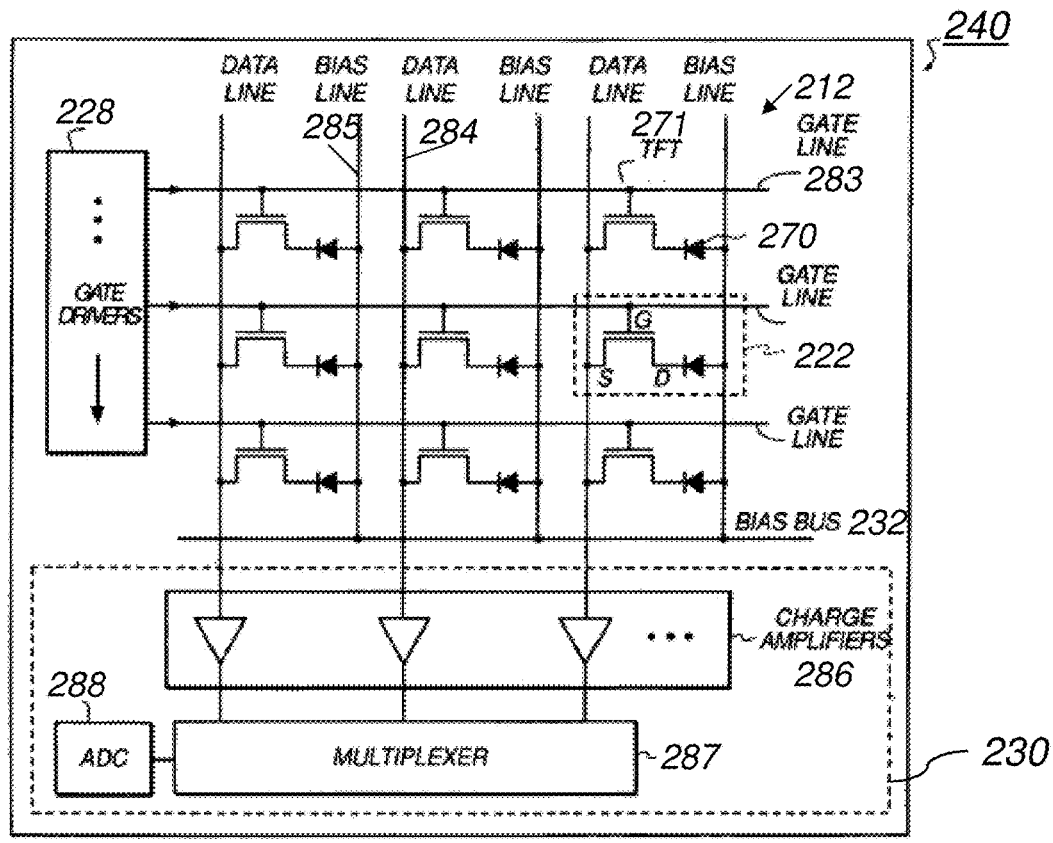
FIG. 2 is a schematic diagram of a photosensor array in a radiographic detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure, which adjacent layers may include a rigid glass layer or a flexible polyimide layer or a layer including carbon fiber without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228.

When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
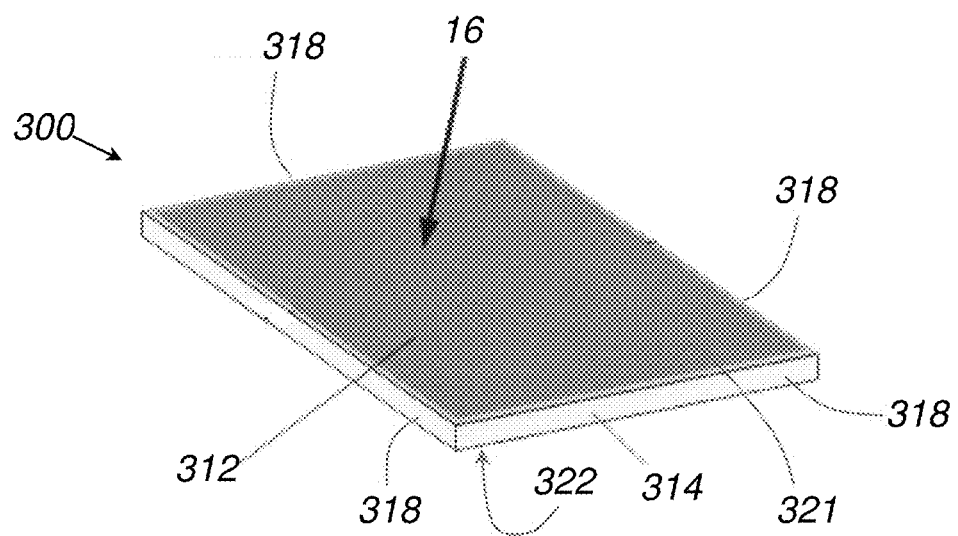
FIG. 3 is a diagram of a DR detector.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
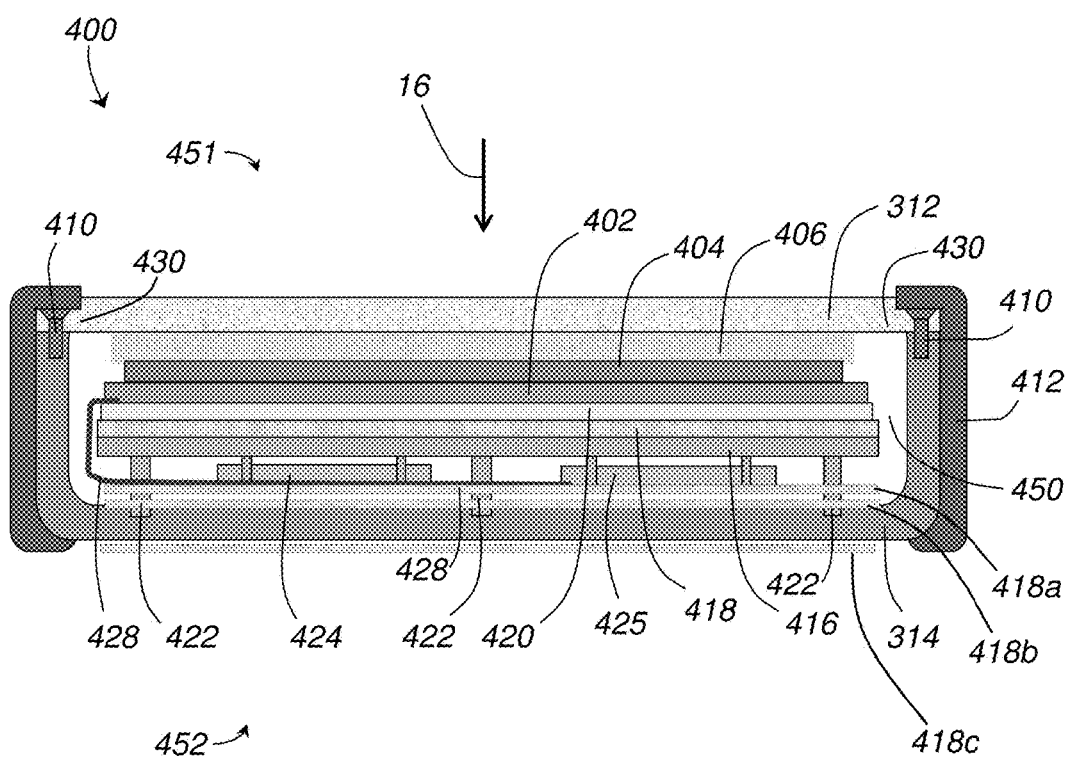
FIG. 4 is cross-section view of the DR detector of FIG. 3.

With reference to FIG. 4, there is illustrated in schematic form an exemplary cross-section view along section 4-4 of the exemplary embodiment of the DR detector 300 (FIG. 3). For spatial reference purposes, one major surface of the DR detector 400 may be referred to as the top side 451 and a second major surface may be referred to as the bottom side 452, as used herein. The multilayer structure may be disposed within the interior volume 450 enclosed by the housing 314 and top cover 312 and may include a flexible curved or planar scintillator layer 404 over a curved or planar the two-dimensional imaging sensor array 12 shown schematically as the device layer 402. The scintillator layer 404 may be directly under (e.g., directly connected to) the substantially planar top cover 312, and the imaging array 402 may be directly under the scintillator 404. Alternatively, a flexible layer 406 may be positioned between the scintillator layer 404 and the top cover 312 as part of the multilayer structure to allow adjustable curvature of the multilayer structure and/or to provide shock absorption. The flexible layer 406 may be selected to provide an amount of flexible support for both the top cover 312 and the scintillator 404, and may comprise a foam rubber type of material. The layers just described comprising the multilayer structure each may generally be formed in a rectangular shape and defined by edges arranged orthogonally and disposed in parallel with an interior side of the edges 318 of the housing 314, as described in reference to FIG. 3.

A substrate layer 420 may be disposed under the imaging array 402, such as a rigid glass layer, in one embodiment, or flexible substrate comprising polyimide or carbon fiber upon which the array of photosensors 402 may be formed to allow adjustable curvature of the array, and may comprise another layer of the multilayer structure. Under the substrate layer 420 a radio-opaque backscatter shield layer 418 may be used as an x-ray scatter blocking layer to help prevent scattering of x-rays passing through the substrate layer 420 as well as to block x-rays reflected from other surfaces in the interior volume 450 or from a region outside of, or exterior, to the detector 400. Readout electronics, including the scanning circuit 28, the read-out circuit 30, the bias circuit 32, and processing system 34a (all of FIG. 1) may be formed adjacent the imaging array 402 or, as shown, may be disposed below frame support member 416 in the form of integrated circuits (ICs) electrically connected to printed circuit boards 424, 425. The imaging array 402 may be electrically connected to the readout electronics 424 (ICs) over a flexible connector 428 which may comprise a plurality of flexible, sealed conductors known as chip-on-film (COF) connectors. A second radio-opaque backscatter shield layer 418a, b, or c may be used as an additional x-ray scatter blocking layer to help prevent scattering of x-rays passing through the detector 400 as well as to block x-rays reflected from other surfaces in the interior volume 450 or from a region outside of, or exterior, to the detector 400. The second backscatter shield layer 418a may be positioned beneath the electronics circuits 424 secured by the frame support beams 422, or attached to a backside of the electronics 424 chips. The second backscatter shield layer 418b may be positioned at the back of the detector on an interior surface of the housing 314, or detector tray, beneath the electronics circuits 424. The second backscatter shield layer 418c may be positioned on an exterior surface of the housing 314, or detector tray. Any one, any two, any three, or more of the radio-opaque backscatter shield layers 418, 418a, 418b, and 418c may be used having selected materials and thicknesses as described herein. Each layer 418, 418a, 418b, and 418c may include one or more different radiopaque materials, as described herein, formed as an alloy, or each layer 418, 418a, 418b, and 418c, may itself include two or more distinct sublayers of different radiopaque materials. Such different sublayers may be mechanically adhered, laminated, or otherwise positioned to abut each other.

X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may connect the multilayer structure to the housing 314 and may further operate as a shock absorber by disposing elastic pads (not shown) between the frame support beams 422 and the housing 314. Fasteners 410 may be used to attach the top cover 312 to the housing 314 and create a seal therebetween in the region 430 where they come into contact. In one embodiment, an external bumper 412 may be attached along the edges 318 of the DR detector 400 to provide additional shock-absorption.

Figure 5:
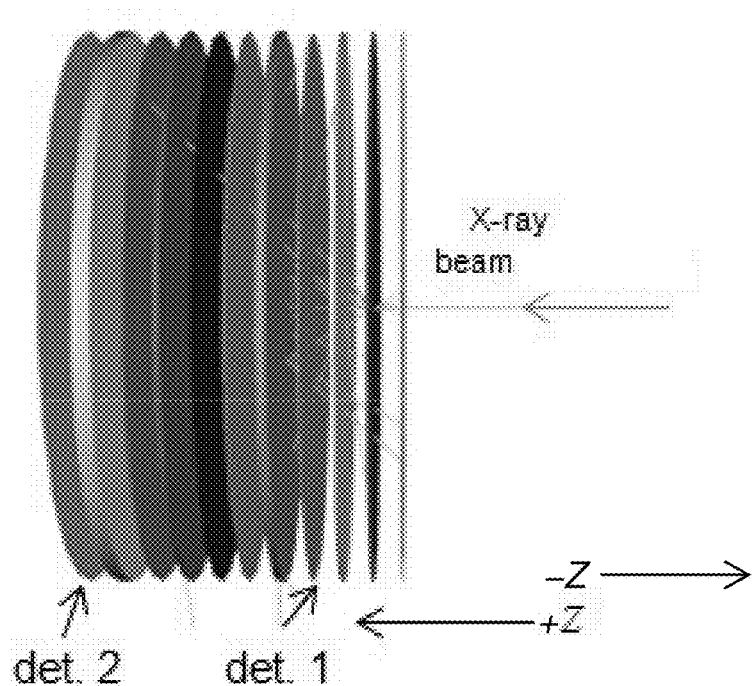
FIG. 5 illustrates exemplary schematics of DR detector geometry used in Geant4 simulations (gaps between material are shown for a better visual representation and are not present during the simulation run)
Figure 6:
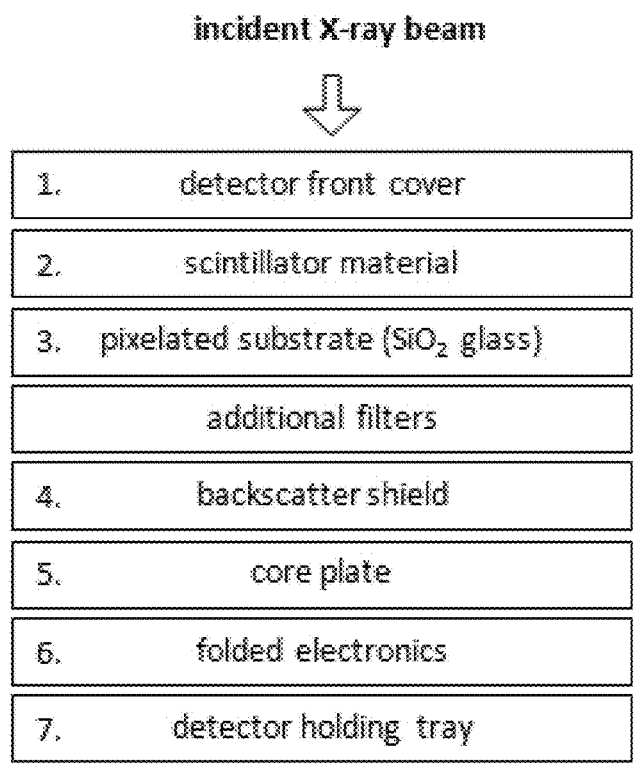
FIG. 6 illustrates an example of a typical DR detector stack configuration used in the Geant4 simulation of FIG. 5.

The Geant4 platform is a simulation toolkit developed by CERN for simulating the passage of particles through matter using Monte Carlo methods. As disclosed herein, simulations were developed to study the physics of X-ray interactions inside of a typical digital radiographic (DR) detector. The yield and direction of emitted radiation was investigated for three exemplary processes: i) photo-electric absorption, ii) characteristic radiation, and iii) Compton and Rayleigh scattering processes. The geometry of the DR detector used in the Geant4 simulation disclosed herein is modeled as shown in FIG. 5. Exemplary elements, or layers, of the DR detector model materials are described in FIG. 6 corresponding to the layers represented in FIG. 5 left-to-right. The developed Geant4 simulations are capable of modeling different combinations of materials used in the DR layers. The toolkit allows switching out (on and off) certain processes such as characteristic radiation, Compton scattering, etc., to detangle processes from each other during simulation runs. The terms "det. 1" and "det. 2" in FIG. 5 refer to placement of simulation detectors for particle measurement and tracking purposes, and do not interact in any way with particles, such as photons. Further tracked characteristics include energy, momentum, coordinates of the interaction, process nomenclature (e.g., name), and other information that allows identification of the process to identify particle yield and direction. Analyses of the simulation results point to advantageous backscatter shield materials, arrangements, thicknesses and methods.

Figure 7A:
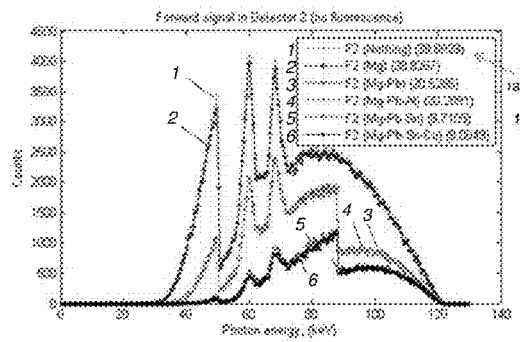
FIGS. 7A-D illustrate exemplary simulated spectral output detected in sensitive detectors 1 and 2 of FIG. 5 with and without characteristic radiation for various stack configurations of the DR detector.
Figure 7C:
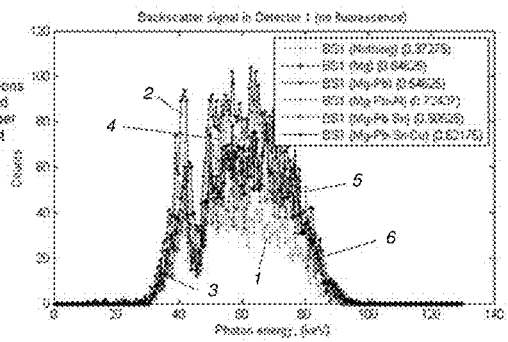
Figure 7B:
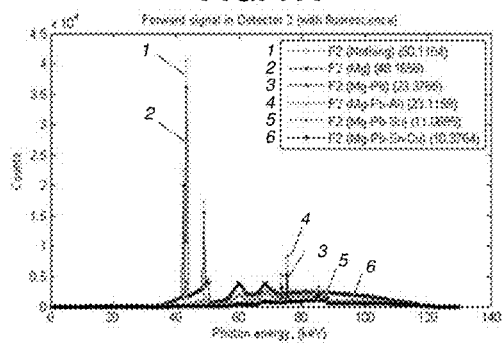
Figure 7D:
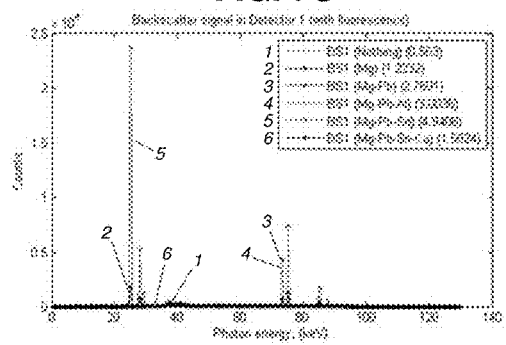
Figure 8A:
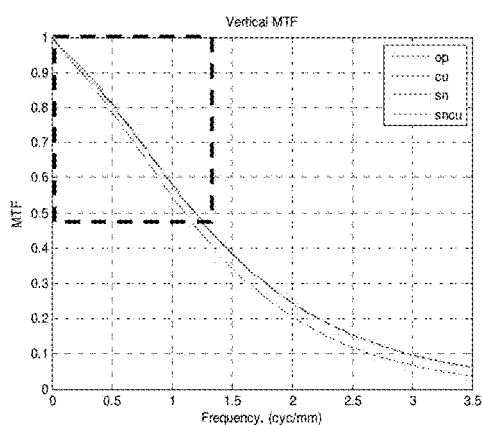
FIGS. 8A-B illustrate modulation transfer function measured at 120 kVp beam condition for a DR detector with various additional filter configurations.
Figure 8B:
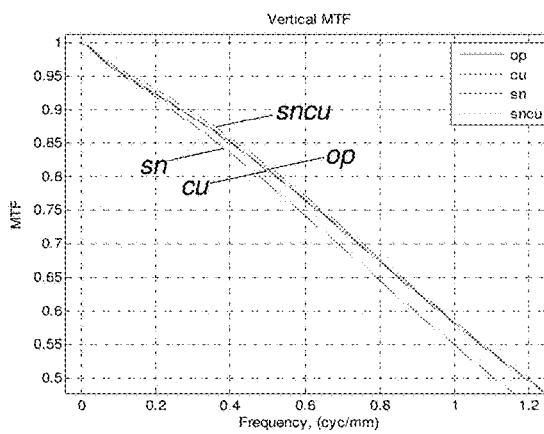

The example of spectra measured in sensitive detectors 1 and 2 (FIG. 5) is shown in FIGS. 7A-D, wherein the plotted backscatter shield material results include (1) no shield; (2) magnesium; (3) magnesium-lead; (4) magnesium-lead-aluminum; (5) magnesium-lead-tin; and (6) magnesium-lead-tin-copper. FIGS. 7A-B show the spectra with and without characteristic radiation detected in a forward direction (along direction of incident X-ray beam, i.e., +z-axis) and backward (−z-axis) directions, respectively. These plots illustrate the relative numbers of absorbed and passed through X-rays in terms of photon counts vs. photon energy in keV. FIGS. 7C-D (also in photon counts vs. photon energy in keV) show the backscattered and reemitted (for example via characteristic process) radiations entering back into the scintillator material layer. In this example, various materials (or filters) were placed between the backscatter shield and the pixel substrate. Their function was to reduce the amount of backscattered and reemitted radiation coming back into scintillator. The (i) front cover, (ii) scintillator, pixelated substrate, (iii) core plate, and (iv) holding plate were modeled as (i) carbon fiber, (ii) gadolinium oxysulfide, (iii) magnesium, and (iv) aluminum, respectively. Two materials, tin and copper, were considered as filters. Tin was placed directly on the backscatter shield followed by a copper filter. While tin was blocking, some amount of backscattered Compton and Raleigh and "backward" emitted characteristic radiation from lead and copper was additionally filtering the described radiation from both lead and tin materials. Tin was chosen to be 300 µm thick and copper 100 µm thick. These thicknesses are exemplary and any other combination of thicknesses and materials may also be used. As observed, tin was able to significantly reduce characteristic K-lines (about 75 and about 86 keV) from lead, although, it added its own characteristic K-lines at about 25 keV. These lines were further attenuated by copper. According to results, the additional placement of lower Z filters (lower atomic number filters) in descendent order from the surface of lead to the pixel substrate surface can effectively suppress unwanted characteristic radiation at beam energies exciting the energy threshold for producing high yield characteristic radiation (e.g., >74 keV for lead K-edge lines) in backscatter shielding material. This was experimentally confirmed, as shown in FIGS. 8A-B, by measuring the modulation transfer function (MTF) for no filter, copper, tin, and tin with copper configurations denoted as "op", "cu", "sn", "sncu" in FIGS. 8A-B, respectively, showing MTF vs. frequency in cyc/mm. As observed, additional tin with copper filtration improves spatial resolution in the low frequency region. The characteristic radiation is created as a result of photo-electric absorption inside of the material. To optimize the material thickness for best suppression of scatter and characteristic radiations, the processes happening inside of the material is pertinent.

Figure 9:
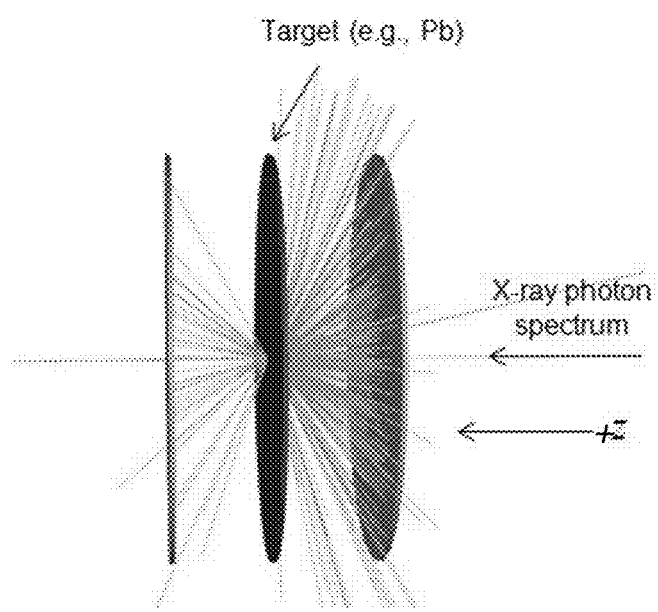
FIG. 9 illustrates an example geometry of a Geant4 simulation with custom particle tracking.
Figure 10A:
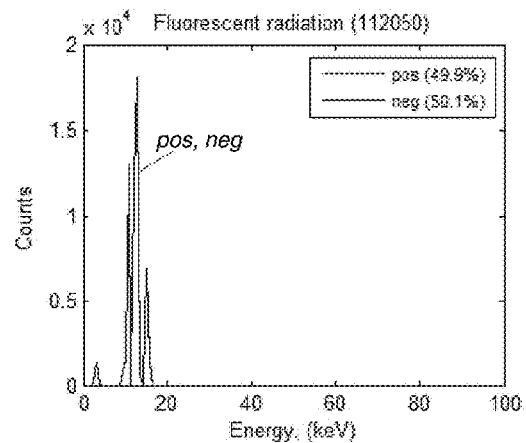
FIGS. 10A-F illustrate exemplary energy spectra histograms of characteristic, Compton, and Rayleigh processes for events generated inside of a target material (FIGS. 10A-C) and events escaped from material boundaries (FIGS. 10D-F)
Figure 10D:
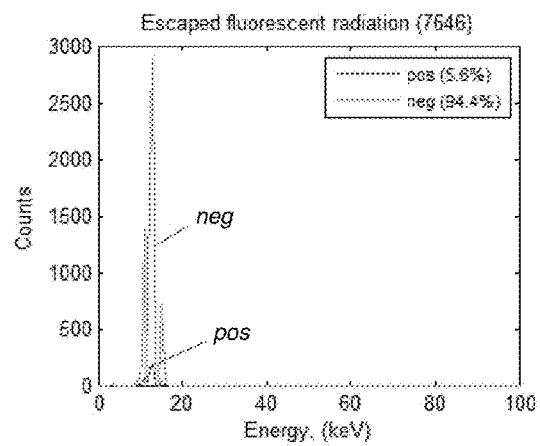
Figure 10B:
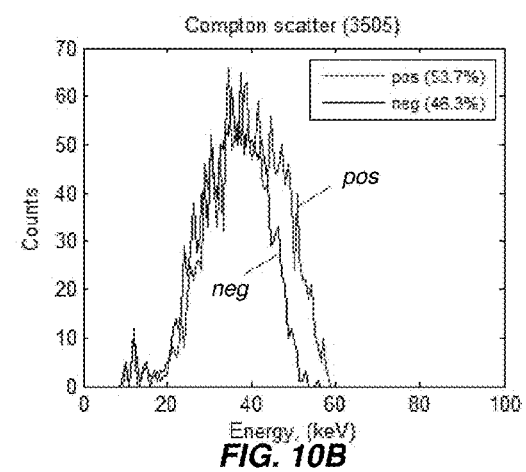
Figure 10E:
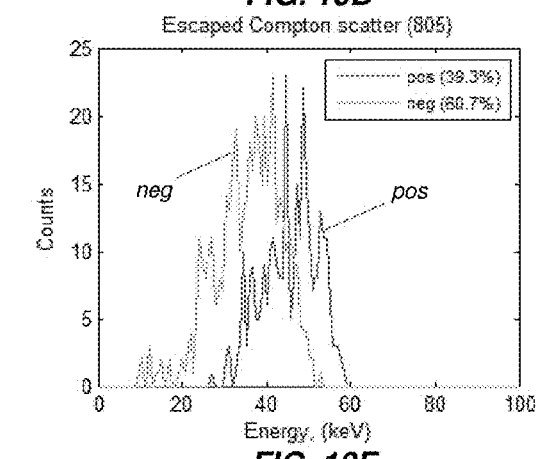
Figure 10C:
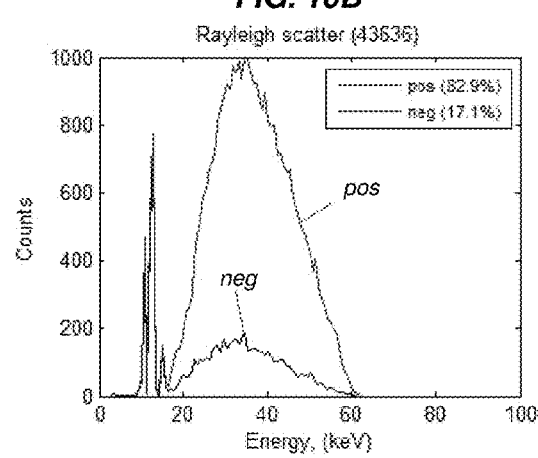
Figure 10F:
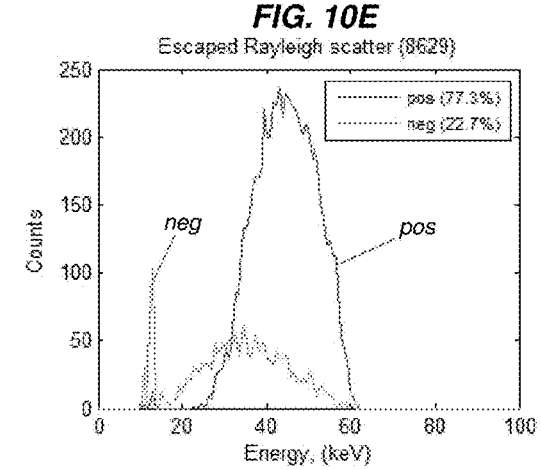
Figure 11A:
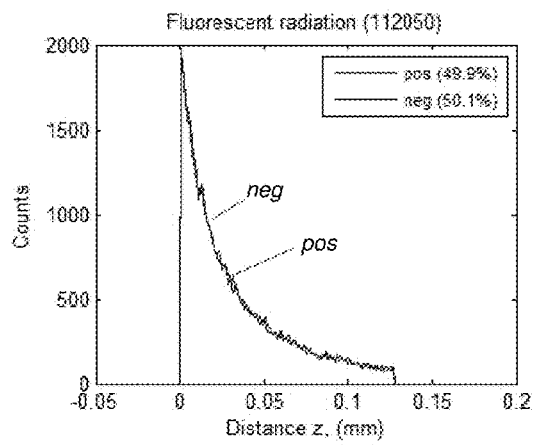
FIGS. 11A-F illustrate exemplary interaction depth histograms of characteristic, Compton, and Rayleigh processes for events generated inside of a target material (FIGS. 11A-C) and events escaped from material boundaries (FIGS. 11D-F)
Figure 11D:
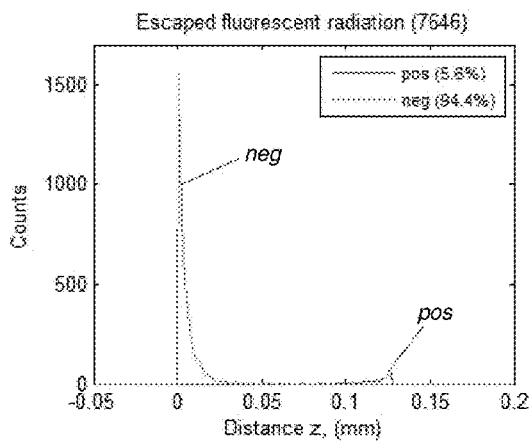
Figure 11B:
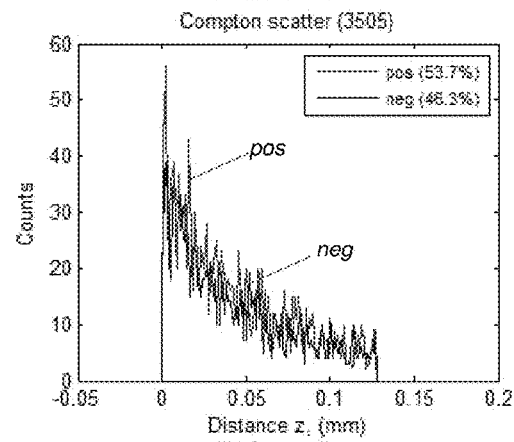
Figure 11E:
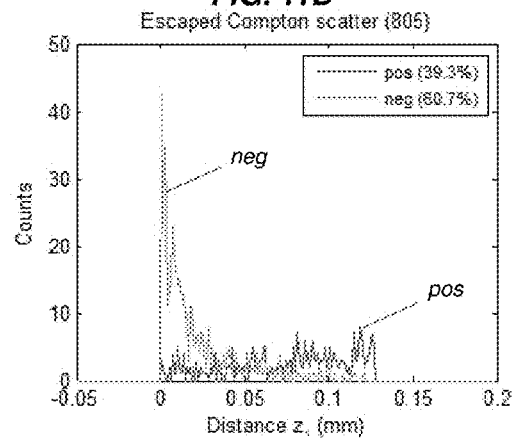
Figure 11C:
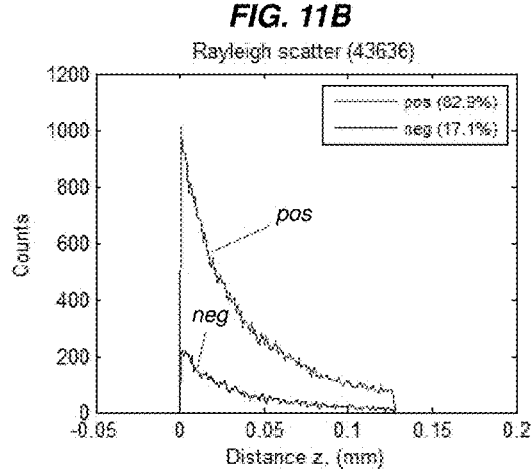
Figure 11F:
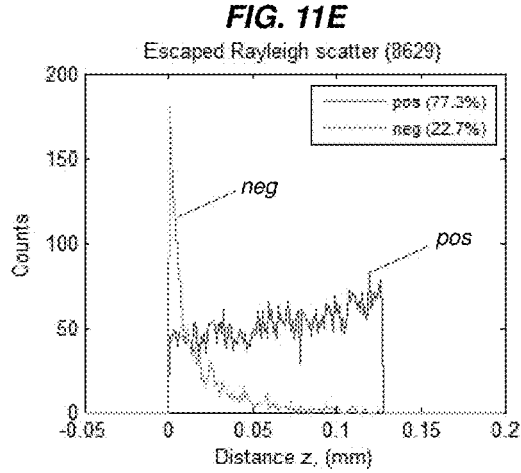
Figure 12A:
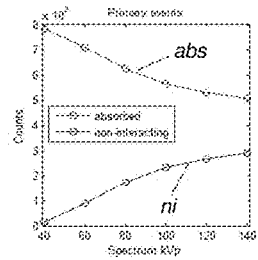
FIGS. 12A-H illustrate exemplary X-ray interaction processes as a function of a kVp of incident X-ray spectra. Events that occurred inside of material are plotted for positive and negative z directions (FIGS. 12A-D), and events that escaped from boundaries of materials are plotted for positive and negative z-directions (FIGS. 12E-H). Lines are also shown representing summation of positive and negative z direction events.
Figure 12B:
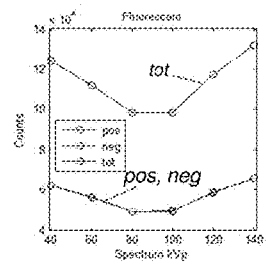
Figure 12C:
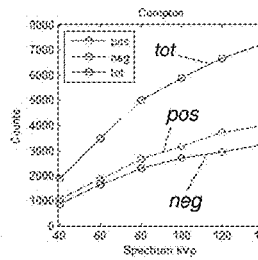
Figure 12D:
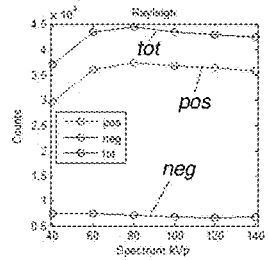
Figure 12E:
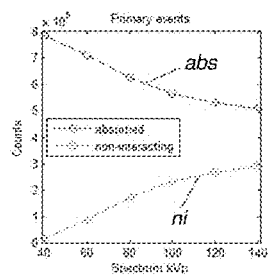
Figure 12F:
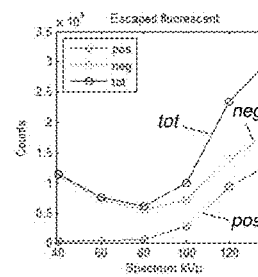
Figure 12G:
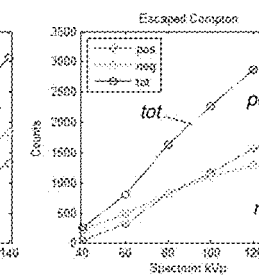
Figure 12H:
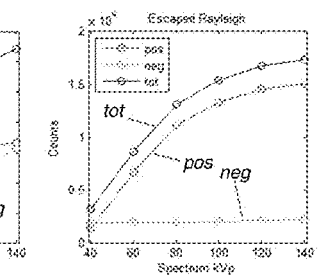
Figure 13A:
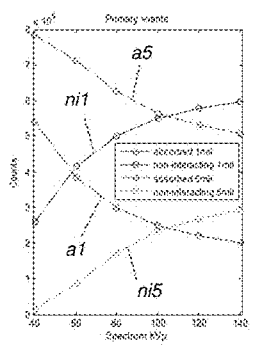
FIGS. 13A-D illustrate exemplary X-ray interaction processes as a function of kVp of incident X-ray spectra plotted for 1 mil and 5 mil of lead material. Numbers presented in the plots are calculated only for events that escaped the boundaries of material.
Figure 13B:
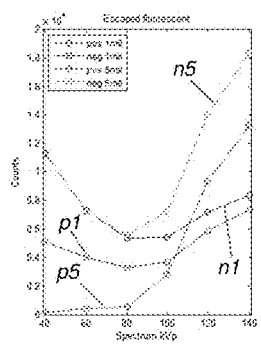
Figure 13C:
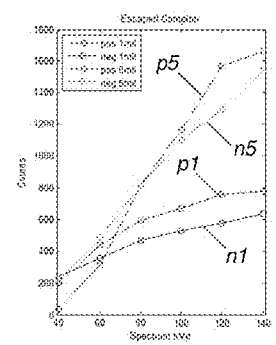
Figure 13D:
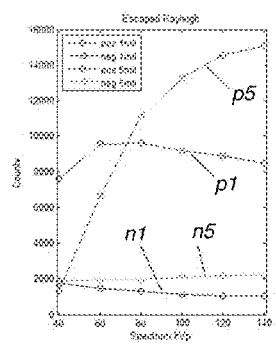

A Geant4 simulation model with custom particle tracking is represented in FIG. 9. In the simulation, the X-ray beam is incident onto a material of selected thickness. Custom particle tracking on both sides of the target, as shown in FIG. 9, identifies radiation process at each step of particle track and records its physics characteristics (energy, momentum, coordinates of interaction, etc.). The results for about 60 kVp (peak) energy using a tungsten anode X-ray spectrum incident on 127 µm of lead (target in center of FIG. 9) are presented in the plots of FIGS. 10A-F, showing photon counts vs. energy in keV. The graphs from top to bottom show characteristic radiation (FIGS. 10A, D), Compton scatter (FIGS. 10B, E), and Rayleigh scatter (FIGS. 10C, F). The energy spectra histograms of these processes are presented in FIGS. 10A-C for events which occur inside of the material. Events occurring with positive z-direction (+z) are plotted together with negative ones (−z). Similar energy spectra histograms for events that escaped material boundaries are plotted in FIGS. 10D-F. FIGS. 11A-F shows histograms analogous to those of FIGS. 10A-F, respectively, but showing photon counts vs. interaction depth in mm plotted in the same scheme analogous to the ones described in FIGS. 10A-F. From FIGS. 10A-F and 11A-F the following conclusions can be made:

1) incident X-ray photons are primarily absorbed at the beginning of material, i.e., closer to the impact surface;
2) incident X-ray photons predominantly undergo elastic scattering by Rayleigh process (Rayleigh yield is about 12 times higher than Compton);
3) in Compton process, lower energy incident photons have higher tendency to scatter back (−z), while forward scattering direction (+z) dominates in the higher energy range (at 60 kVp about 60.7% is scattered back, FIG. 10E);
4) characteristic radiation is emitted equally in positive and negative z directions (i.e., about 50/50, FIG. 10A), however the escaped radiation is primarily directed in negative z direction (94.4%, FIG. 10D).

The conclusions above were derived from simulations for only one kVp X-ray spectrum. It may be beneficial to look at yields of the processes as a function of kVp of incident X-ray spectra. FIGS. 12A-H show simulation results for 128 µm lead illuminated by X-ray spectra of various kVp (photon counts vs. kVp). These results may be summarized as following:

1) characteristic radiation always has higher yield in the backward direction (it's yield is increased at higher kVp spectra due to additional K-lines);
2) Compton scattering becomes more forward directed at higher energies.

Note, the plots do not explicitly display energy dependence, but rather show dependence on beam spectra (i.e., kVp). Energy dependencies can be obtained by simulating monoenergetic incident beams.

The plots shown in FIGS. 13A-D are analogous to those of FIGS. 12E-H (escaped events), shown in photon counts vs. spectrum kVp. They illustrate exemplary X-ray interaction processes plotted for 1 mil and 5 mil of lead material, for absorbed and non-interacting events, where a1 and a5 illustrate results for absorbed, 1 mil of lead, and absorbed, 5 mil of lead, respectively; ni1 and ni5 illustrate results for non-interacting, 1 mil of lead, and non-interacting, 5 mil of lead, respectively; p1 and p5 illustrate results for positive z, 1 mil of lead, and positive z, 5 mil of lead, respectively; and n1 and n5 illustrate results for negative z, 1 mil of lead, and negative z, 5 mil of lead, respectively Numbers presented in the plots are calculated only for events that escaped the boundaries of material. These plots can be summarized as follows:

1) Absorption of incident photons is significantly less in 1 mil of Pb.
2) The non-interacting (not absorbed) events dominate at higher kVp for 1 mil of Pb, while in the case of 5 mil of Pb the majority of incident photons are absorbed.
3) Back illuminated characteristic radiation is almost identical for 1 mil and 5 mil configurations at lower kVp spectra (lower than 80 kVp). Above 80 kVp, the 5 mil configuration is considerably higher, while 1 mil configuration have relatively low yield.
4) The 1 mil configuration produces lower yield in Compton and Rayleigh scattering processes.

In comparison to 5 mil of lead, a 1 mil configuration reduced i) characteristic radiation in both directions and ii) Compton and Rayleigh scatter in both directions, for the expense of having higher number of incident X-ray photons passing through. According to the observed results, the resolution of a detected image may improve if backscatter shielding was made thinner. Although this may be true, objects exterior to the detector can scatter and reemit X-ray radiation back to detector. These X-rays can pass through a thinner backscatter shield more easily than if the shield was thicker.

Figure 14:
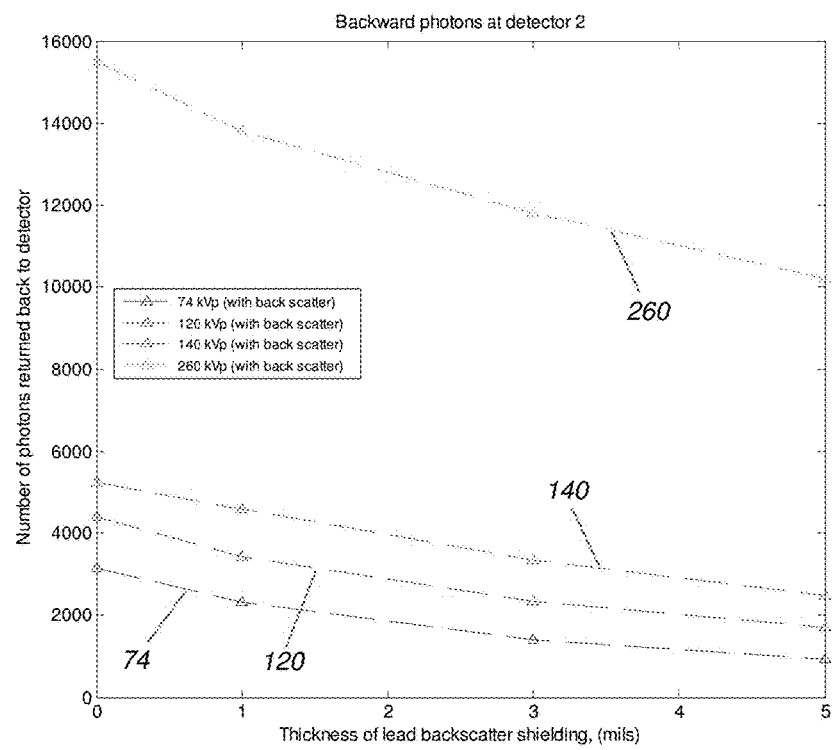
FIG. 14 illustrates exemplary simulated photons returned back to the DR detector as a function of backscatter shielding thickness.

FIG. 14 shows the dependence of the number of photons measured at detector 2 (FIG. 5), e.g., beyond the DR detector layers, traveling in a backward direction (i.e., negative z) as a function of thickness of a lead backscatter shield, in mils. These dependencies are plotted for four different beam conditions (74, 120, 140, and 260 kVp). A simulation exterior environment behind the detector used 43 mils of Cu, 135 mils of Pb, and 600 mils of Fe. As shown in the plot of FIG. 14, a thinner backscatter shield allows more radiation to pass through the detector, scatter and reemit back into the detector from the exterior.

Figure 15:
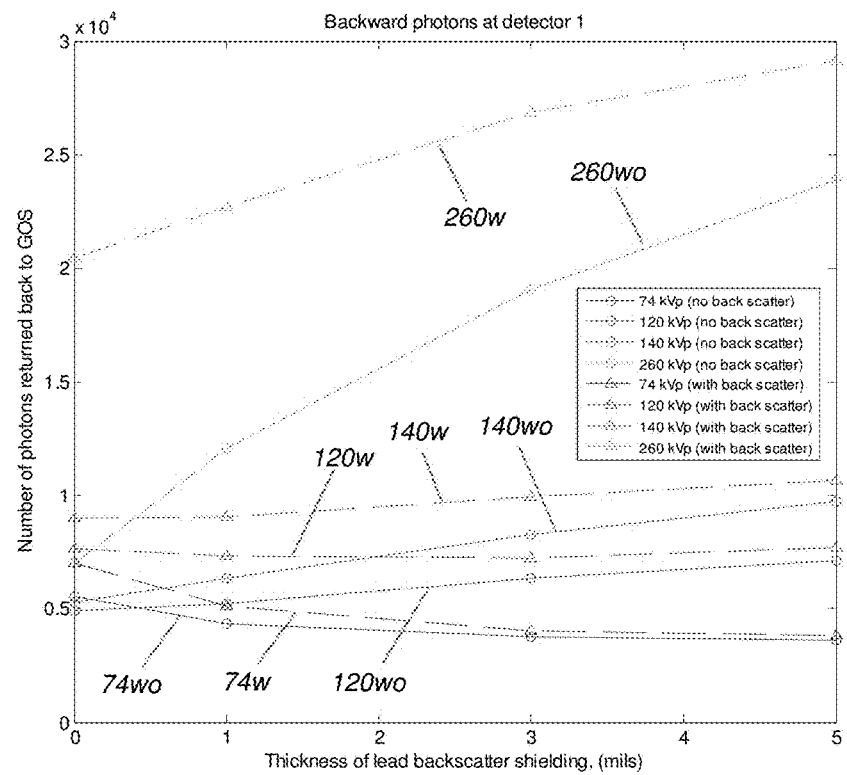
FIG. 15 illustrates exemplary simulated photons returned back to the scintillator material as a function of backscatter shielding thickness. The "no back scatter" mark indicate no objects present behind the DR detector and "with back scatter" mark indicate the presence of exterior materials (for example, Cu, Pb, and Fe).

FIG. 15 shows the number of photons measured at detector 1 (FIG. 5), e.g., behind the scintillator relative to the incident X-ray beam) in the backward negative z direction as a function of backscatter shield thickness, in mils. Plots in the figure were made for the same kVp settings as FIG. 14 (74, 120, 140, and 260 kVp) and also for two cases: with and without simulated exterior objects (designated w and wo). The smaller number of returned photons represent a better result (i.e., less bluring in scintillator MTF). As observed, the thicker backscatter shielding is more effective at lower energies (at least below 80 kVp) in reducing the flux of returned photons for both cases (with and without exterior). As the beam's peak energy exceeds the K-edge excitation energy, thinner backscatter shielding results in lower number of returned photons. This is true for the no-exterior-objects case, however, it changes in the presence of simulated exterior objects described herein. At a 120 kVp beam the optimal backscatter thickness of lead seems to be around 3 mils. When the X-ray peak energy is increased (e.g., to 140 kVp), thinner backscatter shielding becomes beneficial for the cases both with and without exterior objects simulated.

The benefits of the invention disclosed herein include: the backscatter shielding made thinner to minimize the back-emitted characteristic X-ray radiation; the backscatter shielding including at least two layers and placed in the detector such that the first backscatter shield layer would be placed right behind the pixel substrate and the second backscatter layer would be moved to the back of detector for reduction of X-ray photon flux from objects exterior to the detector; additional lower Z materials can be placed between the backscatter shield and the pixelated substrate to suppress back emitted X-ray characteristic radiation produced by the backscatter shield itself; additional filtration can be placed on the back of the detector to suppress backscattered and characteristic radiation from the exterior environment; and the contrast artifact associated with back illumination of detector interior components can be corrected with software by deconvolution of the signal modulated by backscattered and characteristic radiation events initiated by interior components only with known geometry.

In one embodiment, a DR detector has a backscatter shield with thickness selected according to an energy magnitude of radiographic energy received at the detector to minimize the back-emitted X-ray radiation therewithin. At a 120 kVp radiation energy level, a shield having 3 mils of lead may be positioned directly behind the imaging pixel layer. A second shield layer may be positioned at the back of the detector proximate the detector housing. In one embodiment, two layers of lead may include one positioned directly behind the imaging pixels at 1.5 mils and one proximate an interior of the housing at 1.5 mils. Additional shield materials and layers may be positioned between these two lead layers. These additional layers may include one or more materials selected from lower Z materials, i.e., lower atomic number materials than lead, such as tungsten, tin, copper, aluminum, and magnesium, in that order. In one embodiment, lower Z materials are used instead of lead. In one embodiment, no shield layer is used directly behind the imaging pixel layer. Rather, a 3 mil thick lead shield is positioned only at the back of the detector adjacent an interior surface of the housing, or against an exterior surface of the detector housing. In one embodiment, additional lower Z materials positioned between the backscatter shield at the back of the detector and the imaging pixel substrate may be used to suppress back emitted X-ray radiation produced by the backscatter shield itself. In one embodiment, a method of fabricating a DR detector may include determining a magnitude of radiographic energy that will be directed at the DR detector for capturing diagnostic images. A thickness of one or more backscatter shields can be selected based on the magnitude of the radiographic energy. One or more lead shields having a total thickness of about 3 mils can be positioned in the detector for radiographic energies in a range of about 120 kVp or less. In one embodiment, one or more lead shields having a total thickness of about 1-2 mils can be positioned in the detector for radiographic energies in a range of about 125-140 kVp or more. In one embodiment, one or more lead shields having a total thickness of about 5 mils can be positioned in the detector for radiographic energies in a range of about 80 kVp or less. In one embodiment, a shield in the back of the detector abutting an interior surface of the detector may have less thickness than a layer directly behind the imaging pixel layer, such as in a proportion of 1:4. In one embodiment, where an exterior environment of the detector does not contain a significant amount of objects to scatter radiographic energy, one or more lead shields having a total thickness of about 1 mil can be positioned in the detector for radiographic energies in a range of about 80 kVp or less.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A DR detector comprising:
   a layer of imaging pixels;
   a first shield layer behind the layer of imaging pixels, relative to an x-ray source, the first shield layer having a thickness selected according to an energy magnitude of x-ray radiation to be received by the detector to minimize scattered x-ray radiation therewithin;
   a second shield layer behind the first shield layer; and
   a third shield layer between the first shield layer and the second shield layer,
   wherein the third shield layer comprises copper and tin formed as distinct abutting sublayers.

2. The detector of claim 1, wherein the first shield layer comprises a thickness of between about 1 mil and about 5 mils.

3. The detector of claim 2, wherein the second shield layer comprises a thickness of between about 1 mil and about 5 mils.

4. The detector of claim 3, wherein the first shield layer comprises any two or more of the following, in the order listed:
   lead, tungsten, tin, copper, aluminum, and magnesium.

5. The detector of claim 4, wherein the second shield layer comprises any two or more of the following, in the order listed:
   lead, tungsten, tin, copper, aluminum, and magnesium.

6. The detector of claim 3, wherein the second shield layer comprises any two or more of the following, in the order listed:
   lead, tungsten, tin, copper, aluminum, and magnesium.

7. The detector of claim 2, wherein the first shield layer is selected from the group consisting of lead, tungsten, tin, copper, aluminum, and magnesium.

8. The detector of claim 1, wherein the second shield layer comprises a thickness of between about 1 mil and about 5 mils.

9. The detector of claim 8, wherein the second shield layer is selected from the group consisting of lead, tungsten, tin, copper, aluminum, and magnesium.

10. The detector of claim 1, wherein the second shield layer is positioned behind electronic readout circuitry of the detector.

11. The detector of claim 1, wherein the second shield layer is positioned against a back surface of an interior of a housing of the detector.

12. The detector of claim 1, wherein the copper sublayer comprises a thickness between about 50 and 150 µm, and wherein the tin sublayer comprises a thickness between about 225 µm and about 375 µm.

13. The detector of claim 12, wherein the copper sublayer comprises a thickness more preferably about 100 µm, and wherein the tin sublayer comprises a thickness more preferably about 300 µm.

14. The detector of claim 1, wherein the first shield layer comprises any two or more of the following, in the order listed:
    lead, tungsten, tin, copper, aluminum, and magnesium.

15. The detector of claim 14, wherein the second shield layer comprises any two or more of the following, in the order listed:
    lead, tungsten, tin, copper, aluminum, and magnesium.

16. The detector of claim 15, wherein the first shield layer and the second shield layer each comprise a thickness between about 1 mil and about 5 mils.

17. The detector of claim 1, wherein the second shield layer comprises any two or more of the following, in the order listed:
    lead, tungsten, tin, copper, aluminum, and magnesium.

18. A DR detector comprising:
    a layer of imaging pixels;
    a first shield layer behind the layer of imaging pixels, relative to an x-ray source, the first shield layer having a thickness selected according to an energy magnitude of x-ray radiation to be received by the detector to minimize scattered x-ray radiation therewithin;
    a second shield layer behind the first shield layer; and
    a third shield layer between the first shield layer and the second shield layer
   wherein the third shield layer comprises copper and tin formed as an alloy.

19. A DR detector comprising:
    a layer of imaging pixels;
    a first shield layer behind the layer of imaging pixels, relative to an x-ray source, the first shield layer having a thickness selected according to an energy magnitude of x-ray radiation to be received by the detector to minimize scattered x-ray radiation therewithin;
    a second shield layer behind the first shield layer; and
    a third shield layer comprising copper and tin.

* * * * *

UNITED STATES PATENT AND TRADEMARK OFFICE
CERTIFICATE OF CORRECTION

PATENT NO. : 10,236,091 B2
APPLICATION NO. : 15/648582
DATED : March 19, 2019
INVENTOR(S) : Pavlo Baturin Page 1 of 1

It is certified that error appears in the above-identified patent and that said Letters Patent is hereby corrected as shown below:

On the Title Page

Column 1, Item (73), Assignee      Replace "Rcohester" with --Rochester--

Signed and Sealed this
Seventh Day of May, 2019

Andrei Iancu
*Director of the United States Patent and Trademark Office*